(12) United States Patent
Curry et al.

(10) Patent No.: US 8,029,526 B2
(45) Date of Patent: Oct. 4, 2011

(54) COCKING MECHANISM FOR LANCING DEVICE

(75) Inventors: Samuel Mason Curry, Oakland, CA (US); Ray Adams Lathrop, Nashville, TN (US)

(73) Assignee: Abbott Diabetes Care Inc., Alameda, CA (US)

( * ) Notice: Subject to any disclaimer, the term of this patent is extended or adjusted under 35 U.S.C. 154(b) by 408 days.

(21) Appl. No.: 12/191,879

(22) Filed: Aug. 14, 2008

(65) Prior Publication Data

US 2010/0042131 A1    Feb. 18, 2010

(51) Int. Cl.
*A61B 17/14*    (2006.01)

(52) U.S. Cl. ........................................ 606/182

(58) Field of Classification Search ................. 606/181, 606/182, 183; 604/136, 137, 138, 139; 600/573, 600/583; 227/19
See application file for complete search history.

(56) References Cited

U.S. PATENT DOCUMENTS

| | | |
|---|---|---|
| 3,626,929 A | 12/1971 | Sanz et al. |
| 4,577,630 A | 3/1986 | Nitzsche et al. |
| 4,895,147 A | 1/1990 | Bodicky et al. |
| 5,318,584 A | 6/1994 | Lange et al. |
| 5,613,978 A | 3/1997 | Harding |
| 5,730,753 A | 3/1998 | Morita |
| 5,741,288 A | 4/1998 | Rife |
| 5,871,494 A | 2/1999 | Simons et al. |
| 5,873,856 A | 2/1999 | Hjertman et al. |
| 5,944,700 A | 8/1999 | Nguyen et al. |
| 5,984,940 A | 11/1999 | Davis et al. |
| 6,015,392 A | 1/2000 | Douglas et al. |
| 6,022,366 A | 2/2000 | Schraga |
| 6,036,924 A | 3/2000 | Simons et al. |
| 6,045,567 A | 4/2000 | Taylor et al. |
| 6,156,051 A | 12/2000 | Schraga |
| 6,190,398 B1 | 2/2001 | Schraga |
| 6,213,977 B1 | 4/2001 | Hjertman et al. |
| 6,228,100 B1 | 5/2001 | Schraga |
| 6,283,982 B1 | 9/2001 | Levaughn et al. |
| 6,346,114 B1 | 2/2002 | Schraga |
| 6,451,040 B1 | 9/2002 | Purcell |
| 6,530,937 B1 | 3/2003 | Schraga |
| 6,558,402 B1 | 5/2003 | Chelak et al. |
| 6,645,219 B2 | 11/2003 | Roe |
| 6,749,618 B2 | 6/2004 | Levaughn et al. |

(Continued)

FOREIGN PATENT DOCUMENTS

JP    WO2004043258 A1    5/2004

(Continued)

OTHER PUBLICATIONS

PCT International Search Report (Date of Mailing: Nov. 6, 2009); PCT/US2009/053652, filed Aug. 13, 2009.

*Primary Examiner* — S. Thomas Hughes
*Assistant Examiner* — Jonathan W Miles
(74) *Attorney, Agent, or Firm* — Young Basile

(57) ABSTRACT

A lancing device is disclosed in which cocking of the lancet holder is achieved in response to retraction of a push member. A lancing device is also disclosed in which a lancet storage compartment is provided in the housing of the lancing device and closing movement of a closure member for the storage compartment has the effect of cocking the lancet holder. Methods of cocking lancing devices are also disclosed.

9 Claims, 5 Drawing Sheets

U.S. PATENT DOCUMENTS

| | | |
|---|---|---|
| 6,811,557 B2 | 11/2004 | Schraga |
| 6,852,119 B1 | 2/2005 | Abulhaj et al. |
| 6,949,111 B2 | 9/2005 | Schraga |
| 7,105,006 B2 | 9/2006 | Schraga |
| 7,223,276 B2 | 5/2007 | List et al. |
| 2003/0100913 A1 | 5/2003 | Shi |
| 2003/0144609 A1 | 7/2003 | Kennedy |
| 2003/0187470 A1 | 10/2003 | Chelak et al. |
| 2003/0199892 A1 | 10/2003 | Kim |
| 2003/0225430 A1 | 12/2003 | Schraga |
| 2004/0068231 A1 | 4/2004 | Blondeau |
| 2004/0068283 A1 | 4/2004 | Fukuzawa et al. |
| 2004/0127818 A1 | 7/2004 | Roe et al. |
| 2004/0236251 A1 | 11/2004 | Roe et al. |
| 2004/0236362 A1 | 11/2004 | Schraga |
| 2005/0038464 A1 | 2/2005 | Shraga |
| 2005/0090850 A1 | 4/2005 | Thoes et al. |
| 2005/0149089 A1 | 7/2005 | Trissel et al. |
| 2005/0159768 A1 | 7/2005 | Boehm et al. |
| 2005/0234495 A1 | 10/2005 | Schraga |
| 2005/0267505 A9 | 12/2005 | Shraga |
| 2006/0259058 A1 | 11/2006 | Schiff et al. |
| 2007/0049959 A1 | 3/2007 | Feaster et al. |
| 2007/0083222 A1 | 4/2007 | Schraga |
| 2007/0156225 A1 * | 7/2007 | George et al. ................ 623/1.12 |
| 2007/0162063 A1 | 7/2007 | Marshall et al. |
| 2008/0119883 A1 | 5/2008 | Conway et al. |

FOREIGN PATENT DOCUMENTS

WO   WO2005046477   5/2005

* cited by examiner

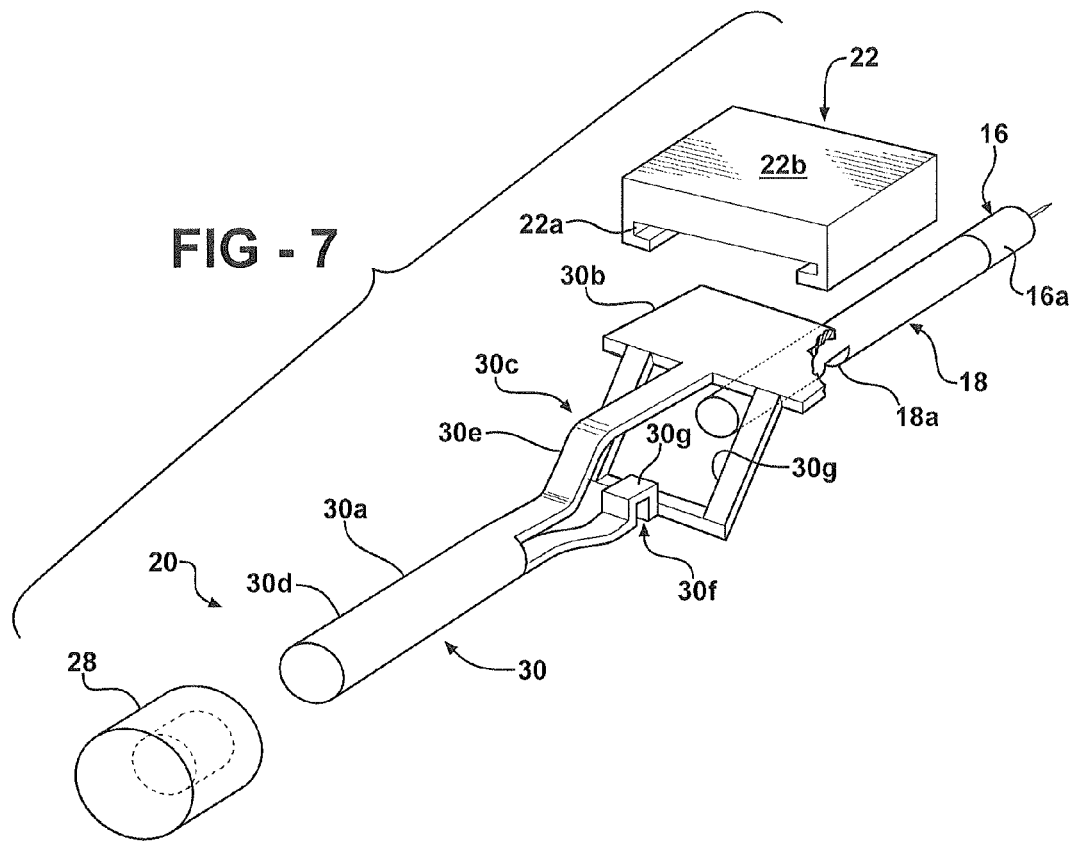
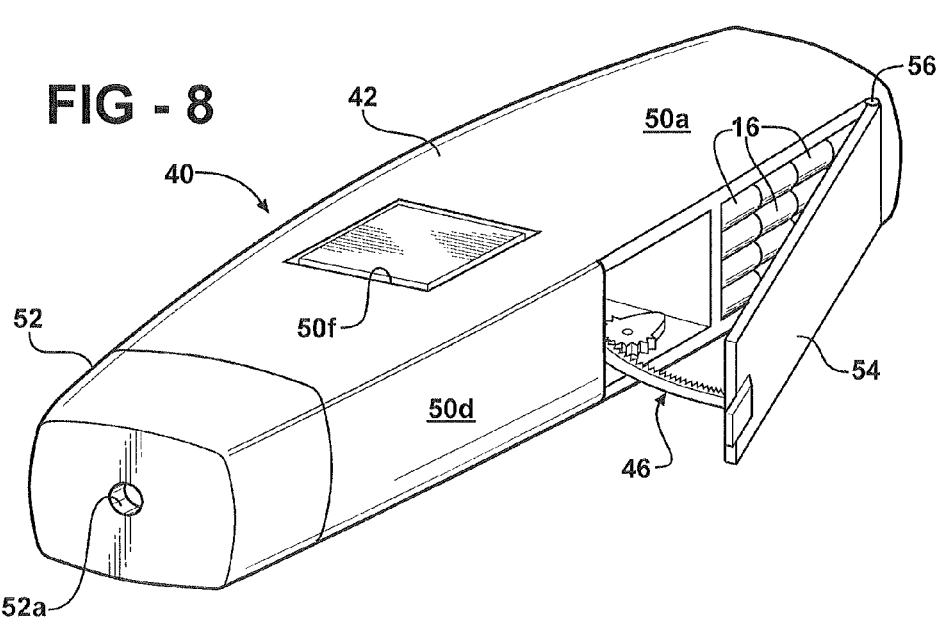

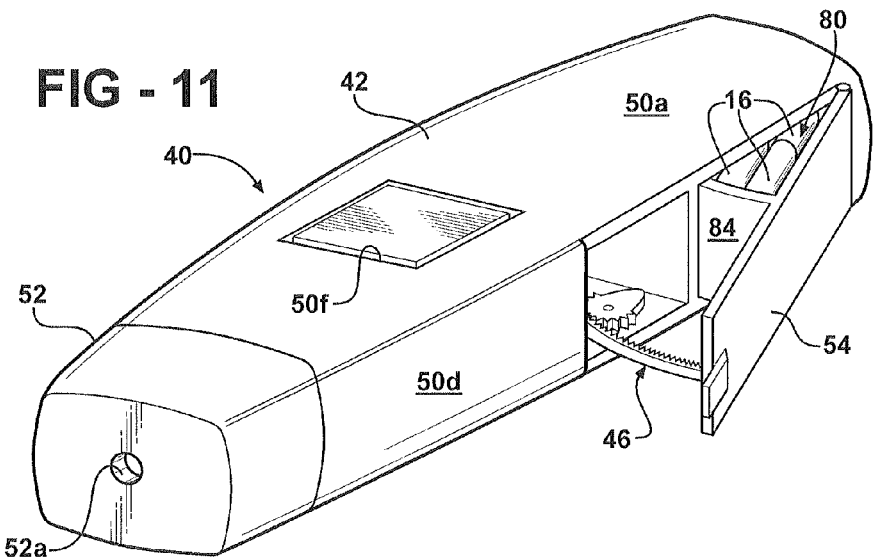
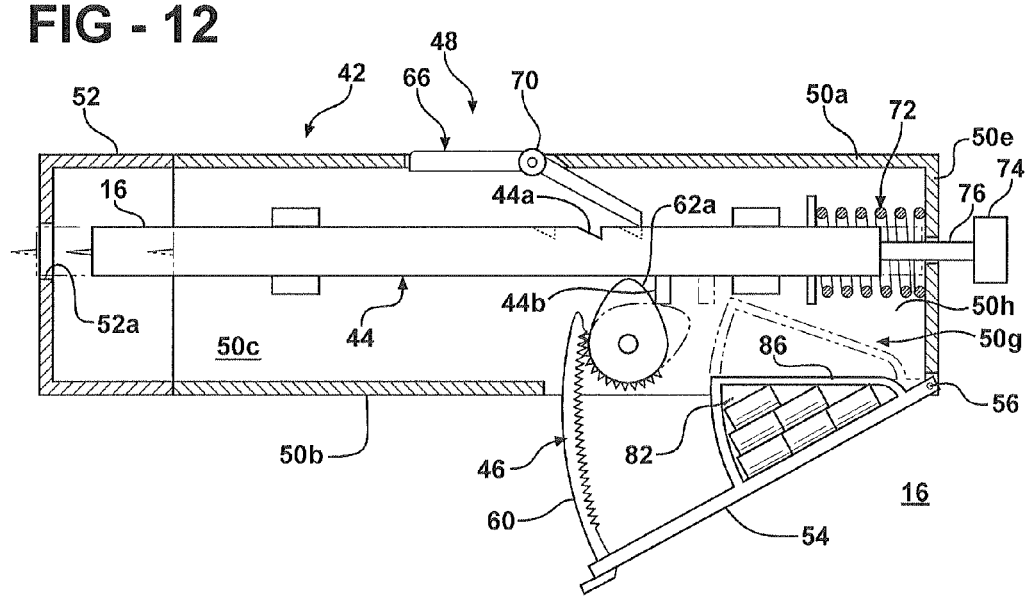

COCKING MECHANISM FOR LANCING DEVICE

BACKGROUND OF THE INVENTION

Lancing devices are typically handheld units that permit users to draw blood for testing and diagnostic purposes. These devices include a housing with a piercing aperture, a lancet that contains one or more needles, and a firing mechanism. The firing mechanism typically includes a spring or other biasing means which can be cocked either by insertion of the lancet or by movement of a cocking member. Once the lancing device is cocked, it is placed against the user's skin, often the fingertip. The user can then press a trigger to actuate the firing mechanism, which momentarily drives the sharp tip of the needle through the piercing aperture to puncture the user's skin and draw blood.

A myriad of lancing devices have been proposed and/or commercialized. Whereas these devices are generally satisfactory, the cocking mechanism tends to be rather complex and expensive and the devices do not provide a storage facility to store the lancets prior to use.

SUMMARY OF THE INVENTION

Embodiments disclosed herein concern a lancing device of the type including an elongated housing; a lancet holder receiving the lancet and mounted for axial movement in the housing between a retracted position and operative position and a cocked position; a cocking mechanism operative to move the lancet holder from its retracted position to its cocked position; and a trigger mounted on the housing and operative to release the lancet holder for movement from the cocked position to the operative position.

In accordance with some embodiments of the invention, a lancing device is disclosed comprising an elongated housing, a lancet, a lancet holder receiving the lancet and configured to move axially in the housing between a retracted position, an extended position, and a cocked position, and a cocking mechanism mounted on the housing and configured to move first inward relative to the housing and subsequently outward relative to the housing. The lancet holder is further configured to move from its retracted position to its cocked position in response to the outward movement of the cocking mechanism. The device also comprises a trigger mounted on the housing and operative to release the lancet holder for movement from the cocked position to the extended position.

In accordance with other embodiments of the invention, a lancing device is disclosed comprising a lancet, a lancet holder configured to receive the lancet and mounted for axial movement in the housing between a retracted position, an extended position, and a cocked position, a lancet storage compartment defined within the housing and sized to accommodate a plurality of lancets, a door configured to move between an open position allowing access to the storage compartment and a closed position preventing access to the storage compartment, a cocking mechanism engaged with the door and configured to move the lancet holder from its retracted position to its cocked position when the door is moved from the open position to the closed position and a trigger mounted on the housing and configured to release the lancet holder to move from the cocked position to the extended position.

In accordance with yet other embodiments of the invention, a method of cocking a lancing device is disclosed. The method, for use with a housing having a lancet holder disposed therein and a storage compartment to accommodate a plurality of lancets, comprises opening a door of the storage compartment to remove or deposit one or more of the plurality of lancets, and closing the door of the storage compartment to cock the lancing device, wherein closing the door of the storage compartment moves the lancet holder from a neutral position to a cocked position.

BRIEF DESCRIPTION OF THE DRAWINGS

The description herein makes reference to the accompanying drawings wherein like reference numerals refer to like parts throughout the several views, and wherein:

FIG. 7 is an exploded perspective view showing a cocking mechanism, a lancet holder, and a trigger employed in the FIG. 1 embodiment;

FIG. 8 is a perspective view of a second embodiment of the invention;

FIG. 11 is a perspective view of a third embodiment of the invention; and

FIG. 12 is a somewhat schematic cross-sectional view of the lancing device of FIG. 11.

DETAILED DESCRIPTION OF THE PREFERRED EMBODIMENT

Figure 1:
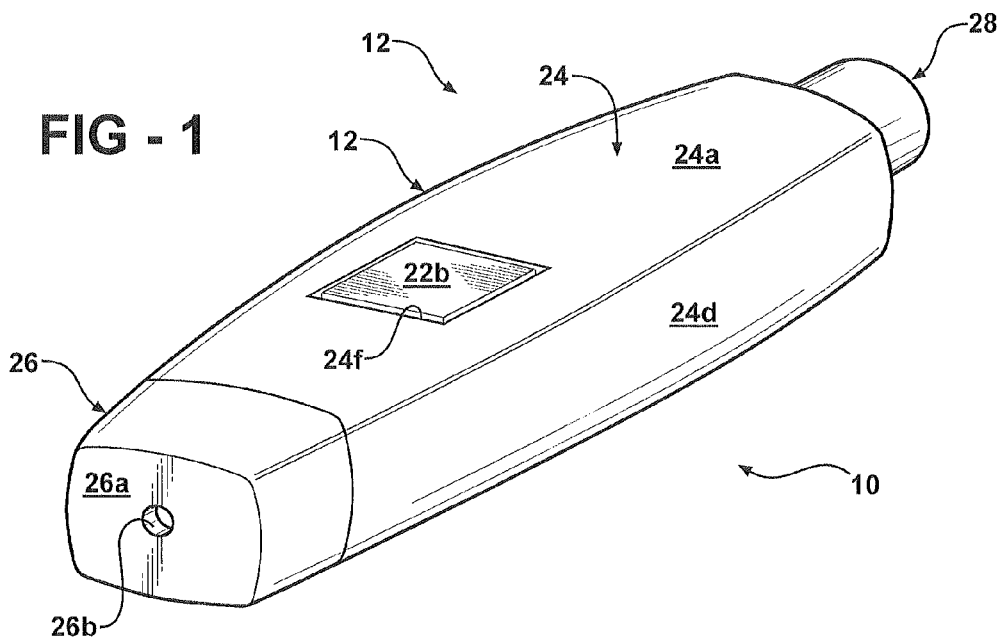
FIG. 1 is a perspective view of a lancing device according to a first embodiment of the invention.

The lancing device 10 seen in FIGS. 1-7 embodiment, broadly considered, includes a housing 12, a lancet 16, a lancet holder 18, a cocking mechanism 20 and a trigger mechanism 22.

Housing 10 includes a main body housing member 24 and a front cap 26.

Main body housing member 24 is elongated, has a generally rectangular cross-sectional configuration, and includes a top wall 24a, a bottom wall 24b, side walls 24c, 24d and a rear end wall 24e. Top wall 24a includes an aperture 24f to accommodate the trigger mechanism.

Front cap 26 is sized to be secured to the front end of housing member 24 and includes a front wall 26a defining a piercing aperture 26b.

Lancet 16 is of known form and includes a generally cylindrical body 16a carrying one or more needles 16b.

Lancet holder 18 comprises a rod suitably mounted for axial movement in the housing and having a notch 18a.

Cocking mechanism 20 includes a button 28 mounted in housing end wall 24e for inward and outward movement relative to the housing end wall and an actuator 30.

Actuator 30 includes a rearward rod portion 30a, a forward guide portion 30b and a central resilient portion 30c.

The rear end 30b of rod portion 36 is fixedly secured in a socket 28a of button 28.

Guide portion 30b has a generally planar configuration. Resilient portion 30c includes an upper resilient arm 30e interconnecting rod portion 30a and guide portion 30b and a lower resilient arm structure 30f further interconnecting rod portion 30a and guide portion 30b. Lower resilient arm structure 30f defines a button 30g and is bifurcated at its forward end to form a window 30h to accommodate axial movement of lancet holder 18.

Trigger mechanism 22 is in the form of a trigger button sized to fit in housing aperture 24f and defining guide structure 22a on the underface of the button for slidable receipt of guide portion 30b of actuator 30.

In assembled relation of the components of the lancing device, button 28 is slidably received in end wall 24e, lancet 16 is suitably mounted on the front end of lancet holder 18, the rear end of actuator rod portion 30a is coupled to button 28, the front planar guide portion 30b of actuator 30 is slidably received in guide structure 22a of trigger 22, and button 30g is resiliently positioned proximate the underside of lancet holder 18.

Figure 2:
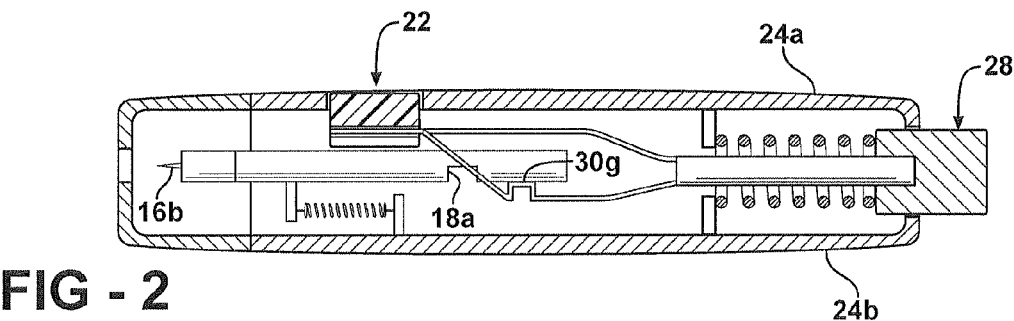
FIGS. 2, 3, 4, 5 and 6 are schematic cross-sectional views of the lancing device of FIG. 1 showing successive steps in the usage of the invention lancing device.
Figure 3:
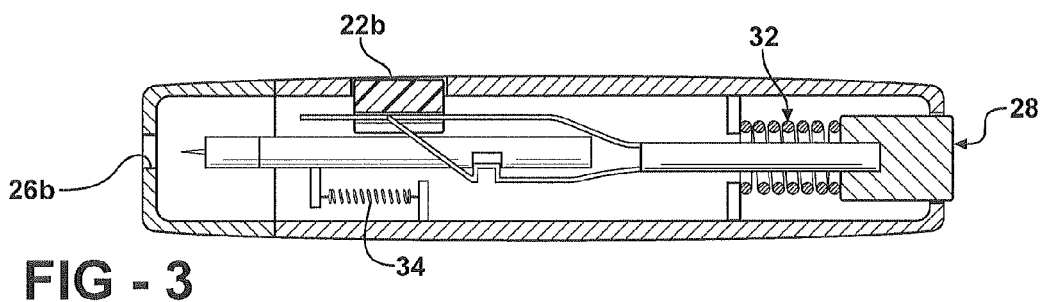
Figure 4:
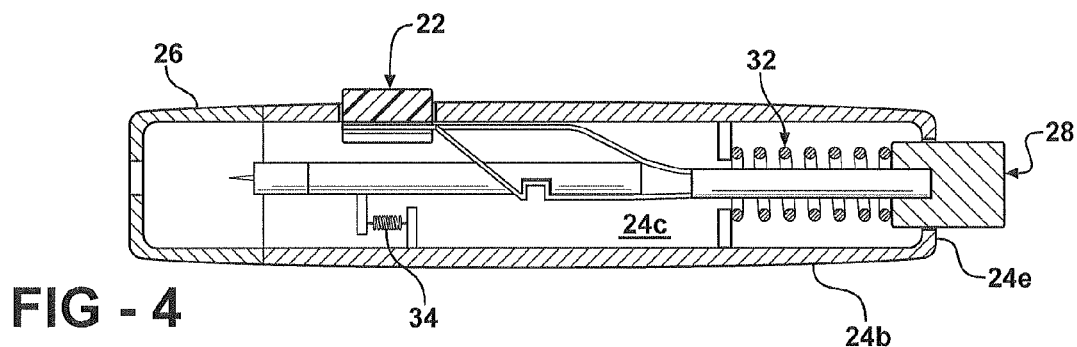
Figure 5:
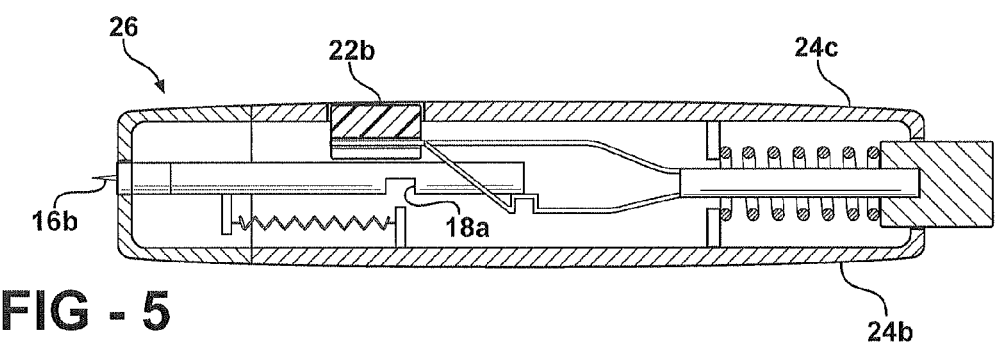
Figure 6:
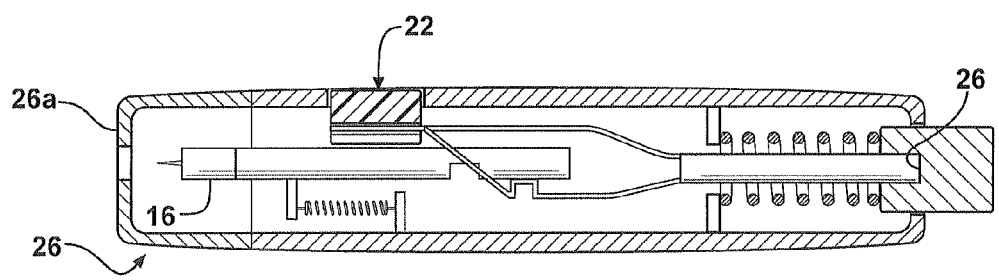

Lancet holder 18 is suitably slidably guided in housing 12 for axial movement between a retracted position seen in FIGS. 2, 3 and 6, a cocked position seen in FIG. 4, and an operative puncturing position seen in FIG. 5.

With initial reference to FIG. 2, showing the device with the lancet holder in its retracted position, button 28 is slidably mounted in housing end wall 24e, the upper face 22b of trigger 22 is flush with the upper face of housing upper wall 24a, and button 30g of actuator 30 is resiliently pressed against the underface of lancet holder 18 rearwardly of notch 18a.

In the transitory position seen in FIG. 3, button 28 has been pressed inwardly or forwardly to move button 30g into alignment with notch 18a with this forward movement of the actuator accommodated by sliding movement of actuator guide portion 30b in trigger guide structure 22a.

When button 30g moves forwardly to a position of alignment with notch 18a the resilient nature of actuator guide portion 30c presses the button into the notch 18a whereupon, following release of button 28, the actuator and lancet holder move rearwardly within the housing under the impetus of, for example, a suitable coil compression spring 30 to the cocked position seen in FIG. 4, wherein the needle 16b of the lancet is, for example, positioned proximate the interface of cap 26 and main body housing member 24 and the upper face 22b of trigger 22 is positioned above the upper face of housing upper wall 24a. This rearward movement of the lancet holder is accompanied by compression of a suitable compression spring mechanism such as shown schematically at 34, the spring device 34 being understood to exert a lesser biasing force than the spring 32 so as not to impede the rearward movement of the actuator and the lancet holder under the bias of spring 32.

Once the lancing device has achieved the cocked position seen in FIG. 4, trigger 22 may be depressed as seen in FIG. 5 to resiliently displace knob 13g from notch 13a and allow the lancet holder and lancet to be fired forwardly under the impetus of spring device 34 to achieve the piercing or puncture position of FIG. 5 wherein a needle 16b extends marginally forwardly of the front wall 26a of cap 26 to achieve the patient piercing function whereafter the lancet and lancet holder retreat to the retracted position seen in FIG. 6, corresponding to the initial position of FIG. 2. As the lancet holder and lancet are fired forwardly, and as seen in FIG. 5, actuator 30 and button 28 undergo a slight rebound movement but thereafter return to their initial retracted position of FIGS. 2 and 6.

The lancing device of the FIGS. 1-7 of the embodiment will be seen to provide a simple effective and inexpensive cocking mechanism.

Figure 9:
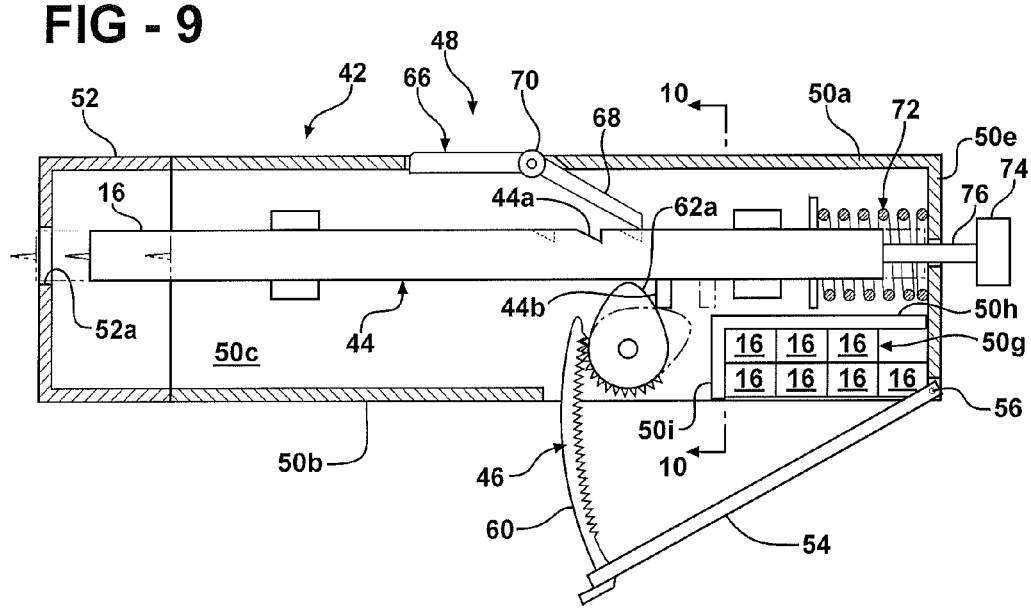
FIG. 9 is a somewhat schematic longitudinal cross-sectional view of the lancing device of FIG. 8.
Figure 10:
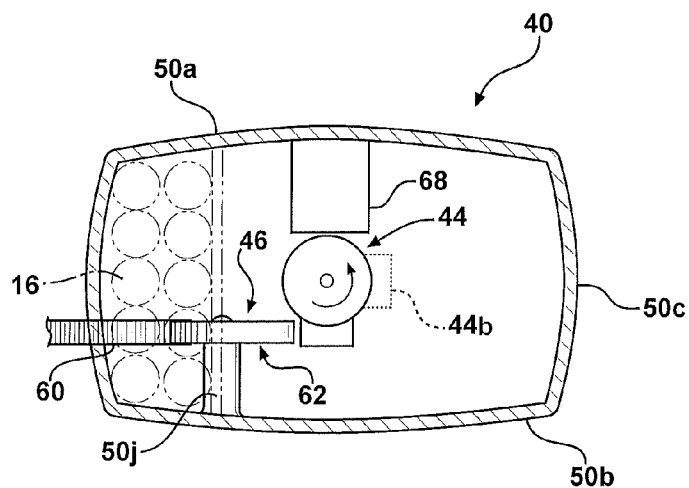
FIG. 10 is a somewhat schematic cross-sectional view taken on line 10-10 of FIG. 9.

The lancing device 40 of the FIGS. 8-10 embodiment, broadly considered, includes a housing 42, a lancet 16, a lancet holder 44, a cocking mechanism 46, and a trigger mechanism 48.

Housing mechanism 42 includes a main body housing member 50 and a front cap 52 defining a piercing aperture 52a.

Main body housing member 24 includes a top wall 50a, a bottom wall 50b, side walls 50c, 50d, and an end wall 50e. Top wall 50a includes an aperture 50f to accommodate trigger mechanism 48.

Main body housing member 50 defines a lancet storage compartment 50g defined by end wall 50e, a longitudinal partition 50h, a transverse partition 50i, and overlying and underlying portions 50a, 50b of top wall 50a and bottom wall 50b, respectively. As seen, compartment 50g is of a size to accommodate a large plurality of lancets 16. Main body housing member 50 further defines a door 54 pivotally mounted about a vertical axis 56 proximate a rear end of the lancing device for movement between an open position, as seen in FIGS. 8 and 9 and a closed position in which access to the lancets is precluded.

Lancet holder 44 has a rod configuration and includes a detent notch 44a and a radial arm 44b.

Lancet holder 44, as seen in FIG. 9, is suitably mounted for axial movement within housing 42 between a retracted position seen in solid lines, a cocked position, and an operative or piercing position.

Cocking mechanism 46 includes an arcuate rack 60 and a pinion 62 mounted for rotation in housing member 50 by a post 50j and having an eccentric portion 62a for coaction with radial arm 44b of lancet holder 44.

Trigger mechanism 48 is schematically illustrated and may, for example, include a trigger member 66 positioned in housing aperture 50f and a detent mechanism 68 biased downwardly against lancet holder 44 via a suitable spring mechanism 70. With the lancet holder 18 in the solid line retracted position, and with reference to FIG. 9, closing movement of door 54 has the effect of moving the lancet holder to its cocked position. Specifically, as the door 54 is moved from its open to its closed position, arcuate rack 60 meshingly engages pinion 62 to rotate the pinion and bring eccentric portions 62a into engagement with lancet holder radial arm 44b to move the lancet holder rearwardly within the housing against the resistance of a coil spring 72. The parameters of the device are chosen such that as eccentric portion 62a clears radial arm 44b, detent 68 moves into detented engagement with notch 44a so that the lancet holder is held in its cocked position whereafter, upon depression of trigger mechanism 66 to release detent 68 from engagement with notch 44a, the lancet holder is free to move forwardly under the urging of spring 72 to achieve the piercing position. Note that in this position, since radial arm 44b has now moved forwardly to a position in the path of radial movement of eccentric portion 62a of pinion 62, door 54 cannot be opened to allow access to the lancets without a specific operation on the part of the user to take the arm 44b out of the path of movement of eccentric portion 62a. This may be done, for example, as shown in FIG. 9 by attaching a knob 74 to the rear end of lancet holder 18 via a shaft 76 passing through housing end wall 50e. With this arrangement, knob 74 may be turned to rotate lancet holder 44 within the housing to move radial arm 44b out of the path of eccentric portion 62a and allow the door 54 to be opened to allow access to the lancet storage compartment.

The lancing device of the FIGS. 8-10 embodiment will be seen to provide a convenient arrangement for storing lancets, allow access to the storage compartment to be coordinated with cocking of the lancet holder, and provide a safety feature in the sense that unauthorized or inadvertent access to the stored lancets is discouraged by requiring a specific user operation to allow unlocking of the access door to the lancet storage compartment.

The lancing device of the FIGS. 11 and 12 embodiment is generally similar to the FIG. 8-10 embodiment with the exception that the lancet storage compartment, rather than being defined within the housing by walls of the housing, is defined as an integral part of the door 54 and moves inwardly and outwardly with the door.

Specifically, the lancet storage compartment 80 of the FIGS. 11 and 12 embodiment is constituted as a drawer carried by the door 54 and is defined by the door, as the drawer face, by a floor 82, an arcuate end wall 84, and a partition 86.

With this construction, as the door 54 is moved to its open position, the lancets positioned in the storage compartment 80 are moved outwardly of the housing to a position wherein they can be readily accessed from the open upper end of compartment 80.

A method of cocking the lancing device 40 disclosed with reference to FIGS. 8-12 comprises opening a door 54 of the storage compartment 50g to remove or deposit one or more of the plurality of lancets 16 and closing the door 54 of the storage compartment 50g to cock the lancing device 40, wherein closing the door 54 of the storage compartment 50g moves the lancet holder 44 from a neutral position to a cocked position. The step of closing the door can operate a cocking mechanism 46, for example, having a rack mounted within the housing on the door and a pinion driven by the rack engaging the lancet holder. The door 54 can be configured to pivot between the open and closed positions. The door 54 can be further configured to pivot about an axis on one edge of the door proximate a rear end wall of the housing. The lancet storage compartment 50g can be a drawer and the door 54 can be the drawer face.

The above-mentioned embodiments have been described in order to allow easy understanding of the present invention. The invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A lancing device comprising:
    a lancet;
    a housing defining a piercing aperture;
    a lancet holder configured to receive the lancet through the piercing aperture and mounted for axial movement in the housing between a retracted position, an extended position, and a cocked position;
    an arm extending radially from the lancet holder;
    a lancet storage compartment defined with walls within the housing and configured to store a plurality of lancets;
    a door configured to move between an open position allowing access to the lancet storage compartment and a closed position preventing access to the lancet storage compartment;
    a cocking mechanism having a rack carried by the door and a pinion mounted on the housing and configured to move the lancet holder from its retracted position to its cocked position when the door is moved from the open position to the closed position such that the pinion engages the arm of the lancet holder;
    a trigger mounted on the housing and configured to release the lancet holder to move from the cocked position to the extended position; and
    a knob extending through a rear end of the housing and configured to move the arm out of contact with the pinion.

2. The lancing device according to claim 1 wherein the lancet holder is operative in response to movement of the door from its open position to its closed position.

3. The lancing device according to claim 1 wherein the door is mounted for pivotal movement on the housing between the open and closed positions.

4. The lancing device according to claim 3, wherein the door is configured to rotatably open about a pivot axis on one end of the door proximate an end of the housing opposite the piercing aperture.

5. The lancing device according to claim 1, wherein the lancet storage compartment is a drawer and the door is a drawer face, wherein the drawer slidably opens when the drawer face is opened and the drawer slidably closes when the drawer face is closed.

6. A method of using a lancing device comprised of a housing having a lancet holder disposed therein and configured to receive a lancet through a piercing aperture in the housing, the lancet holder mounted for axial movement in the housing between a retracted position, an extended position, and a cocked position, the housing having a storage compartment defined by walls within the housing to accommodate a plurality of lancets, the method comprising:
    opening a door of the storage compartment to remove or deposit one or more of the plurality of lancets;
    cocking the lancing device, the cocking comprising:
        closing the door of the storage compartment to move a pinion mounted on the housing with a rack carried by the door, wherein closing the door of the storage compartment moves the lancet holder from a neutral position to a cocked position by moving the pinion to engage an arm extending radially from the lancet holder; and
    rotating a knob extending through a rear end of the housing to move the arm out of contact with the pinion to allow for access to the storage compartment.

7. The method of claim 6, wherein the door is configured to pivot between the open and closed positions.

8. The method of claim 7, wherein the door is configured to pivot about an axis on one edge of the door proximate a rear end wall of the housing.

9. The method of claim 6, wherein the lancet storage compartment is a drawer and the door is the drawer face.

* * * * *